United States Patent [19]

Farris

[11] 4,021,200

[45] May 3, 1977

[54] ELECTRONIC DIGITAL RADIAL AND ELECTRO IMMUNODIFFUSION CALIBRATING VIEWER

[76] Inventor: Walter Farris, 19193 Parkside, Detroit, Mich. 48221

[22] Filed: Sept. 29, 1975

[21] Appl. No.: 617,322

[52] U.S. Cl. .............................. 23/253 R; 33/1 BB; 356/157; 356/171
[51] Int. Cl.² ................. G01B 11/02; G01N 33/16
[58] Field of Search ............. 23/253 R; 73/432 PS; 356/102, 169, 170, 171, 156, 157; 33/1 L, 1 C, 1 BB, 262, 277, 278, 280, 282, 298

[56] References Cited

UNITED STATES PATENTS

| | | | |
|---|---|---|---|
| 2,301,935 | 11/1942 | Ehringhaus | 356/170 |
| 3,001,081 | 9/1961 | Bower | 356/169 |
| 3,776,817 | 12/1973 | VanDerPfordten | 23/253 R X |
| 3,843,450 | 10/1974 | Saxholm | 23/253 R X |
| 3,905,767 | 9/1975 | Morris et al. | 23/253 R X |

OTHER PUBLICATIONS

Oxford Diffu–Gen System for Immunodiffusion, Oxford Laboratories, Inc., 4 pp. (1975).

Primary Examiner—Robert M. Reese
Attorney, Agent, or Firm—Edward M. Apple

[57] ABSTRACT

A viewer, with electronic digital read out display, and calibrated to measure either a radial immunodiffusion or an electrophoresis rocket type protrusion.

9 Claims, 6 Drawing Figures

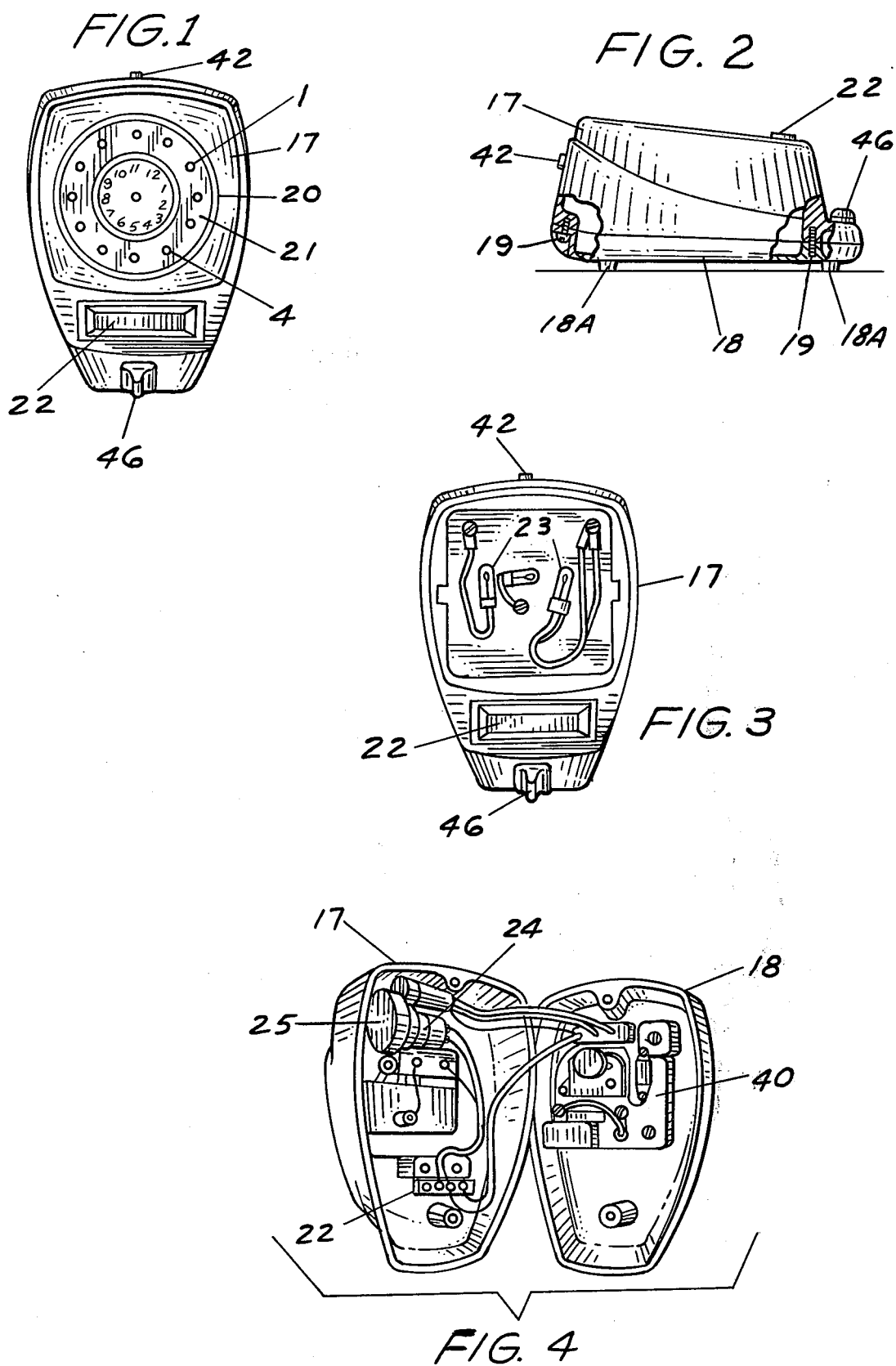

ELECTRONIC DIGITAL RADIAL AND ELECTRO IMMUNODIFFUSION CALIBRATING VIEWER

This invention relates to medical laboratory, clinical, or research equipmentand equipment and particular reference to a device for accurately measuring the visually displaying the magnitude of a radial, immunodiffusion or an electrophoresis protrusion on a glass or plastic plate, such as is used in the examination of blood samples and the like.

An object of the invention is the provision of an electronic device which will give a digital read out of the results of an immunodiffusion test.

Another object of the invention is to provide a compact, portable viewer, which automatically displays the results of an immunodiffusion test, without the necessity of using manual measuring and actuating means.

Another object of the invention is to provide an electronic digital device, which will accomodate diagnostic plates of different shapes, sizes, and components.

A further object of the invention is to provide a device which can be used to estimate all proteins having an electrophoretic mobility, which differs from that of the antibodies incorporated in the agar gel with which conventional diagnostic plates are treated.

Another object of the invention is to provide an electronic digital display device for obtaining a highly accurate measurement of immunodiffusion precipition rings, such are produced according to the teachings of Mancini, Carbonara and Heremans, as reported in Immunochemistry 2:235, 1965, wherein it was established that protein antigens diffuse to an accurate end point and no further.

The foregoing and other objects and advantages of the invention will become more apparent as the description proceeds, reference being made from time to time to the accompanying drawings, forming part of the within disclosure in which drawings:

FIG. 1 is a top plan view of a device embodying the invention.

FIG. 2 is a left side elevation of the device shown in FIG. 1.

FIG. 3 is a top plan view of the device shown in FIG. 1, with the bezel removed and the illuminating elements exposed.

FIG. 4 is perspective view of the top and bottom sections, adjusted from one another to show the arrangements of internal parts.

Figure 5:
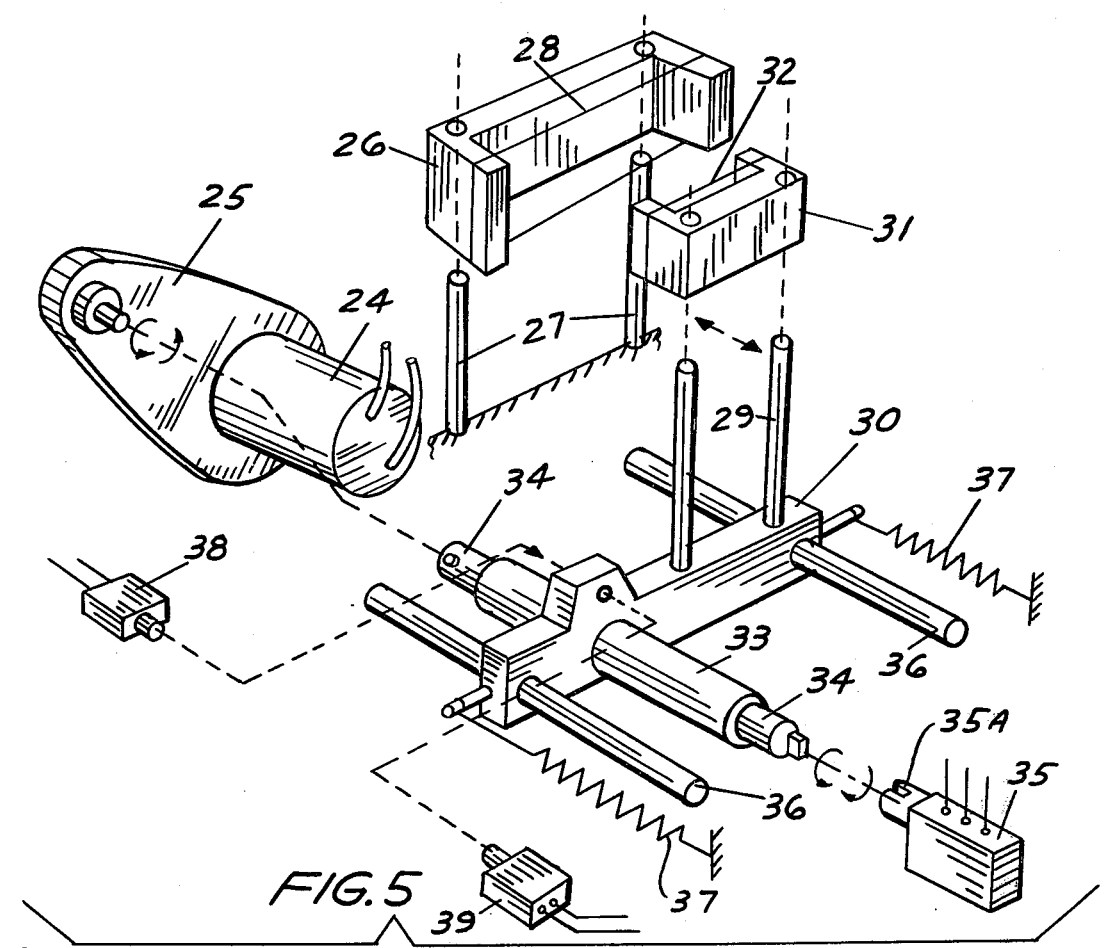
FIG. 5 is an exploded view of certain of the working parts housed in the top section of the device.

Referring now more particularly to the drawings, it will be understood that in the embodiment herein disclosed, the reference character 17 indicates the top section of the device and 18 indicates the base section, which are secured together by machine screws 19, or other suitable means. (FIG. 2) The base 18 is provided with rubber supports 18A.

The top section 17 of the device (FIG. 1) carries a removable bezel 20 which supports a Radial Immuno-Diffusion (RID) plate 21, which is treated with an agar gel as manufactured and distributed by Behring Diagnostics, a department of Hoechst Pharmaceuticals Inc., of Somerville, New Jersey. The bezel 20 may be replaced with a rectangular shaped bezel (not shown) which is adapted to receive an ElectroImmunoDiffusion (EID) plate, such as manufactured and distributed by the same company.

The agar gel on the plates is formed with a multiplicity of wells numbered 1-12 (FIG. 1) in which samples of blood or the like to be tested are deposited, following the teachings of Mancini, Carbonara and Heremans, as disclosed in Immuno Chemistry 2.235, 1965.

The purpose of the instant invention is to give an accurate digital read out display of the extent of the radial diffusion of the precipition protrusion of the antigens during the tests. The digital read out is displayed on the digital panel 22 as hereinafter described.

Figure 6:
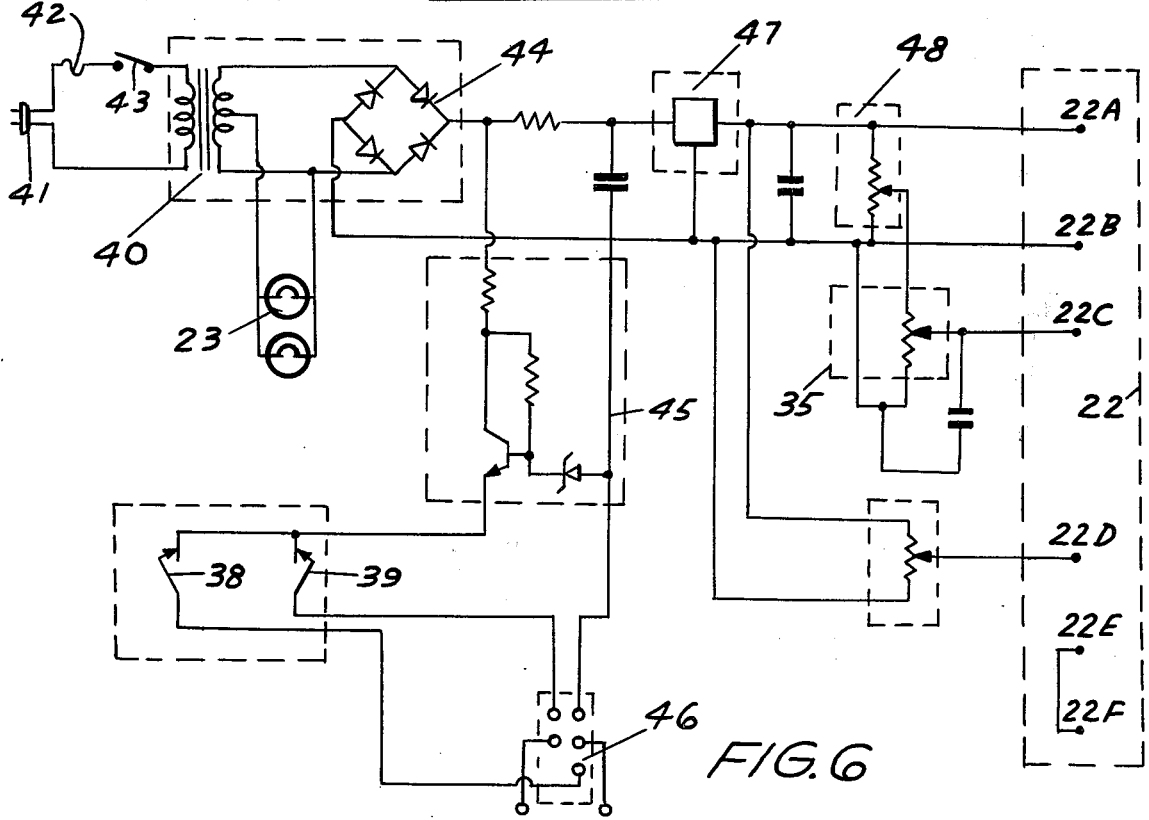
FIG. 6 is a wiring diagram of the electrical circuit employed in the device.

Immediately beneath the bezel 20, I provide suitable illuminating elements 23, which are wired into the electrical circuits as shown in FIG. 6. Although I show incandescent lamps (FIG. 3), it will be understood that I can use fluorescent tubes with equal facility.

The top section 17, also houses the principal working parts of the device (FIG. 5) which comprise a reversible electric motor 24, a reduction gear box 25, a fixed cross hair support 26, (FIG. 5) which is mounted on posts 27, and carries a cross hair 28.

Mounted on posts 29, carried by a walking arm 30, is a moveable cross hair support 31, which supports a moveable cross hair 32, which is arranged to vertically align with the fixed cross hair 28 as hereinafter described.

The walking arm 30 has an internally threaded member 33 which engages the external threads (not shown) of a drive shaft 34, which connects at one end with the output spindle of the gear box 25, and at the other end connects to the rotatable insert 35A, of a travel sensitive, twenty turn potentiometer 35, which is electrically connected in the circuits as shown in FIG. 5. The walking arm 30 is guided by rods 36 and is urged toward the potentiometer 35 by springs 37. A pair of normally closed limit switches 38 and 39 are actuated by the walking arm 30 and limit the forward and reverse movements of the arm 30 and the moveable cross hair support 31. The motor 24, the potentiometer 35 and the limit switches 38 and 39 are connected in the electrical circuits as shown in FIG. 6.

The base section 18 (FIG. 4) supports a transformer 40 and other electrical components, all of which are shown in FIGS. 4 and 6. The transformer 40 (FIG. 6) receives 110 Volt AC power supply as at 41, through a fuse 42 and switch 43 and transforms the 110 V into various lesser voltages used in the operation of the device.

From the transformer 40, 6.3 AC voltage goes to the illumination bulbs 23 and 12.6 AC voltage goes through a diode bridge 44 where it is changed to DC voltage for the motor power supply controls 45, and through the normally closed limit switches 38 and 39 to the motor drive double pole, double throw reversing switch 46. Current also flows through the diode bridge 44 to a meter regulator 47, a meter scale 48, the travel sensing potentiometer 35 and to a conventional digital panel meter 22, which is programmed to read out zero to ten centimeters and on which pins 22A, B, C and D signal input to the digital panel and pins 22E and 22F indicate the decimal point on the digital panel.

AS the drive shaft 34 of the motor 24 rotates the support arm 31 carrying the moveable cross hair 32 closer to, or farther away from, the stationary cross hair 28, the potentiometer 35 proportionately varying resistance. The varying resistance is calibrated through the electronic circuits to produce the digital read out on the panel 22 which accurately indicates the relative position of the cross hairs 28 and 32.

OPERATION

The device operates as follows: When an unknown amount of antigen is allowed to diffuse radically from a well (1–12) in a uniform thin layer of agar on an RID plate, containing antibodies having a specificity for the antigen, the final area reached by the radial precipitate is directly proportional to the amount of antigen added. After a radial immunodiffusion (RID) plate 21 has incubated for a specific period of time, it is then placed on the invention device. The main switch 43 is then placed in the "on" position to supply current to illuminate the measuring area. Move the reversing switch 46 to the left so that the cross hairs 28 and 32 are vertically aligned. The (RID) plate 21 is then rotated so that the left edge of the radial precipitate is in alignment with the aligned cross hairs 28 and 32. Next move to the right the switch 46 which controls the motor 24, until the mobile cross hair 32 aligns with the right side of the radial precipitate. The true diameter of the radial precipitate will then be displayed on the digital panel 22 in centimeters.

The protrusion of an electro-phoresis test may likewise be measured.

Having described my invention what I claim and desire to secure by Letters Patent is:

1. A device for measuring and displaying the magnitude of an immunodiffusion test, comprising in combination a base member and a top member, said top member having a pair of cross hairs, one of which is stationary and the other of which in moveable, a digital meter panel for indicating relative movement of said moveable cross hair, motor means to move said moveable cross hair, eletrical circuits connected to said motor means, and a potentiometer in said circuits and responsive to the movement of said moveable cross hair for effecting a digital read out on said digital panel.

2. The structure of claim 1, in which said potentiometer is arranged to raise and lower the resistance in said circuits upon the movement of said cross hair, whereby to effect the read out on said digital panel.

3. The structure of claim 1, including means on said base for transforming and regulating the flow of current through said cicuits and said potentiometer.

4. The structure of claim 1, including means to effect the forward and reverse movement of said moveable cross hair.

5. The structure of claim 1, in which there are limit switches in one of said circuits, which switches are actuated by the forward and reverse travel of said moveable cross hair.

6. The structure of claim 1, including an immunodiffusion plate supported on said top member, and arranged to be scanned by said moveable cross hair.

7. The structure of claim 6, including means in said circuits for illuminating said immunodiffusion plate and said cross hairs.

8. The structure of claim 1, in which said cross hairs are carried on supports, one of which is moveable, said last named support being mounted on a threaded arm, and a threaded shaft driven by said motor engaging said arm.

9. The structure of claim 8, in which said threaded shaft engages said potentiometer to cause an increase or decrease of resistance to the flow of electrical energy through said potentiometer, the variance or resistance being in proportion to the travel of said arm on said shaft and registered on the said digital panel.

* * * * *